United States Patent [19]

Taira

[11] Patent Number: 4,982,726
[45] Date of Patent: Jan. 8, 1991

[54] ELECTRONIC ENDOSCOPE SYSTEM WITH SUCTION CHANNEL OF CONTROLLABLE STRENGTH OF SUCTION

[75] Inventor: Daijiro Taira, Tochigi, Japan

[73] Assignee: Kabushiki Kaisha Toshiba, Kawasaki, Japan

[21] Appl. No.: 510,243

[22] Filed: Apr. 18, 1990

[30] Foreign Application Priority Data

Apr. 20, 1989 [JP] Japan .................................. 1-98853

[51] Int. Cl.$^5$ .............................................. A61B 1/00
[52] U.S. Cl. ...................................................... 128/4
[58] Field of Search ........................................ 128/4, 6

[56] References Cited

U.S. PATENT DOCUMENTS

| | | | |
|---|---|---|---|
| 4,402,310 | 9/1983 | Kimura | 128/4 |
| 4,509,507 | 4/1985 | Yabe | 128/4 |
| 4,844,052 | 7/1989 | Iwakoshi et al. | 128/4 |
| 4,852,551 | 8/1989 | Opie et al. | 128/4 |
| 4,919,113 | 4/1990 | Sakamoto et al. | 128/4 |

*Primary Examiner*—William H. Grieb
*Attorney, Agent, or Firm*—Foley & Lardner, Schwartz, Jeffery, Schwaab, Mack, Blumenthal & Evans

[57] ABSTRACT

An electronic endoscope system equipped with a suction channel, capable of freely adusting the inhalation strength of the suction channel. The system includes a suction switch to be pressed by an operator for indicating a desired strength of inhalation through th esuction channel by an extent of depression; a sensor for dtecting the extend of depression of the suction switch; a pinching valve for adjusting a strength of inhalation through the suction channel by adjustably changing an extend of opening; and a controlling unit for controlling the strength of inhalation through the suction channel to the desired strength of inhalation through the suction channel indicated by the suction swtich, by adjusting the extend of opening of the pinching valve in accordance with the extent of depression of the suction switch detected by the sensor.

6 Claims, 3 Drawing Sheets

ELECTRONIC ENDOSCOPE SYSTEM WITH SUCTION CHANNEL OF CONTROLLABLE STRENGTH OF SUCTION

BACKGROUND OF THE INVENTION

1. Field of the Invention

The present invention relates to an endoscope system equipped with a suction channel for inhaling air from an end of a scope section of the endoscope system.

2. Description of the Background Art

A conventional electronic endoscope system equipped with a suction channel for inhaling air from an end of a scope section of the endoscope system has been that in which the turning on and off of the inhalation is controlled by opening and closing of an electromagnetic pinching valve, such that when a suction switch provided on the scope grip portion is pressed down by an operator, the electromagnetic pinching valve is opened and the inhalation at a prescribed inhalation strength is started, whereas when the suction switch is released, the electromagnetic pinching valve is closed and the inhalation stops.

Because of this ON/OFF control at two levels, it has been impossible for a conventional electronic endoscope system equipped with a suction channel to adjust the inhalation strength freely, as had been possible for an old fashioned endoscope equipped with a mechanical valve structure in which the valve had been operated manually through a control lever.

SUMMARY OF THE INVENTION

It is therefore an object of the present invention to provide an electronic endoscope system equipped with a suction channel, capable of freely adjusting the inhalation strength of the suction channel.

This object is achieved by the present invention by providing an electronic endoscope system, comprising: a scope section having an end portion; suction pump means for providing a power for inhalation; suction channel means for providing a path for inhalation by the suction pump means from the end portion of the scope section; suction switch means to be pressed by an operator for indicating a desired strength of inhalation through the suction channel means by an extent of depression; sensor means for detecting the extent of depression of the suction switch means; pinching valve means, located on the suction channel means between the end portion of the scope section and the suction pump means, for adjusting a strength of inhalation through the suction channel means by adjustably changing an extent of opening; and means for controlling the strength of inhalation through the suction channel means to the desired strength of inhalation through the suctuon channel means indicated by the suction switch means, by adjusting the extent of opening of the pinching valve means in accordance with the extent of depression of the suction switch means detected by the sensor means.

Other features and advantages of the present invention will become apparent from the following description taken in conjunction with the accompanying drawings.

DETAILED DESCRIPTION OF THE PREFERRED EMBODIMENTS

Figure 1:
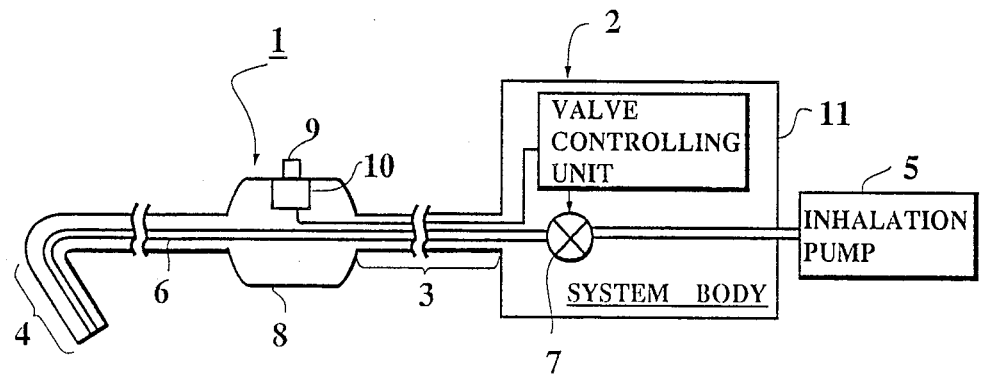
FIG. 1 is a schematic block diagram of one embodiment of an electronic endoscope system according to the present invention.

Referring now to FIG. 1, there is shown one embodiment of an electronic endoscope system according to the present invention.

This electronic endoscope system generally comprises a scope section 1 and a system body 2, connected through a joint cord 3. From an end portion 4 of the scope section through the joint cord 3 and the system body 2 to a suction pump 5 annexed to the system body 5, there is provided a suction channel 6.

Inside the system body 2, a pinching valve 7 is provided on the suction pump 6, and opening and closing of this pinching valve 7 is adjustably controlled by a valve controlling unit 11 connected to the pinching valve 7 inside the system body 2.

Figure 2:
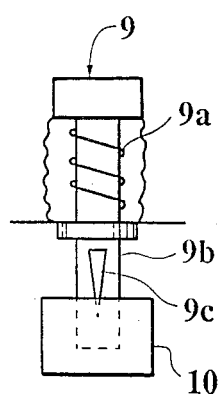
FIGS. 2(A) and (B) are front and side views of a suction switch in the system of FIG. 1 for explaining its operation.
Figure 2:
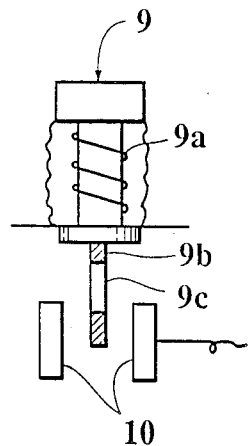

On the scope grip portion 8 of the scope section 1, a suction switch 9 and a photo interrupter 10 are provided. As shown in FIGS. 2(A) and 2(B), this suction switch 9 comprises a spring 9a wound around a rod 9b, where the rod 9b has a triangular window 9c on its lower part thrusted into the photo interrupter 10. Thus, according to how much the suction switch 9 is pressed down by an operator, a different amount of light can be transmitted through the photo interrupter 10, so that an extent of depression of the suction switch 9 can be determined from an interruption signal outputted by the photo interrupter 10. Such an interruption signal of the photo interrupter 10 is provided to the valve controlling unit 11, so as to control an extent of opening of the pinching valve 7 in accordance with an extent of depression of the suction switch 9.

When an electromagnetic valve is employed as the pinching valve 7, the valve controlling unit 11 can be constructed as follows.

Figure 3:
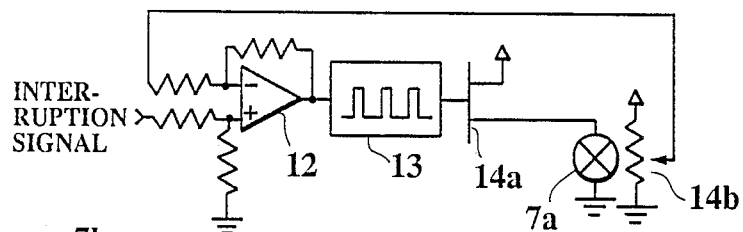
FIG. 3 is a schematic circuit diagram for a valve controlling unit in the system of FIG. 1, for a case of using an electromagnetic valve as a pinching valve.

Namely, as shown in FIG. 3, the valve controlling unit 11 in this case comprises a feed-back circuit formed by an operational amplifier 12, a pulse width modulator 13, a valve driver 14a, and a valve opening detector 14b. The interruption signal and a feed-back signal from the valve opening detector 14b are fed into the operational amplifier 12, so that an output of the operational amplifier 12 is proportional to a voltage difference between the interruption signal and the feed-back signal. Then, the pulse width modifier 13 is controlled by this output of the operational amplifier 12, so as to voltage control the valve driver 14a to control the extent of opening of the electromagnetic valve 7a in accordance with an extent of depression of the suction switch 9.

Figure 4:
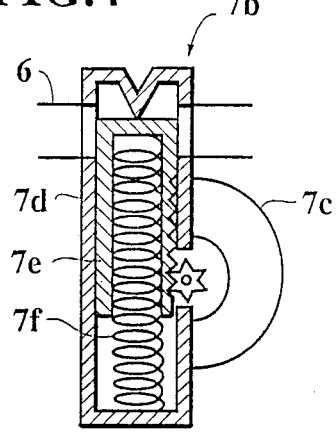
FIG. 4 is an illustration of a stepping motor driven valve that may be utilized in the system of FIG. 1.

Alternatively, a stepping motor driven valve such as that shown in FIG. 4 may be employed as the pinching valve 7. In this stepping motor driven valve 7b of FIG. 4, the suction channel 6 is attached to an outer frame 7d, and inside the outer frame 7d, an inner frame 7e with a spring 7f attached is slidably placed, such that when the inner frame is at the highest position, the sucton channel 6 is completely closed, whereas when the inner frame is at the lowest position, the suction channel 6 is fully open. The inner frame 7e slides inside the outer frame 7d as a stepping motor 7c engaging to the inner frame 7e rotates. The stepping motor 7c is capable of rotating a prescribed amount of angle in either direction each time.

Now, when such a stepping motor driven valve 7b is employed as the pinching valve 7, the valve controlling unit 11 can be constructed as follows.

Figure 5:
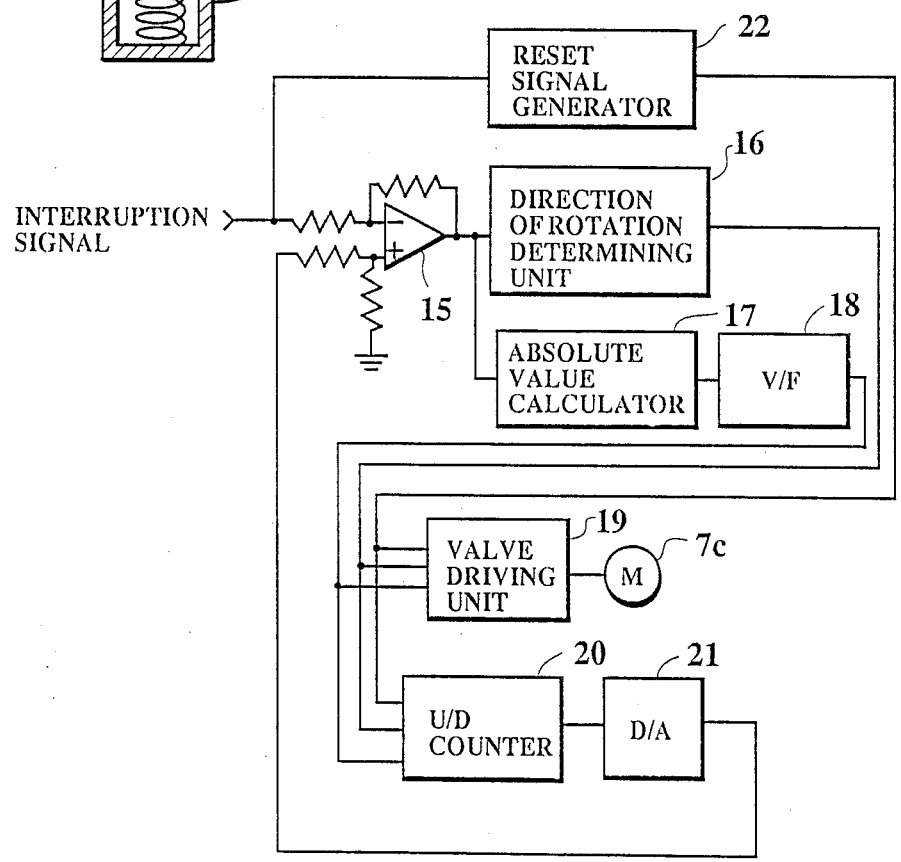
FIG. 5 is a schematic circuit diagram for a valve controlling unit in the system of FIG. 1, for a case of using a stepping motor driven valve of FIG. 4 as a pinching valve.

Namely, as shown in FIG. 5, the valve controlling unit 11 in this case comprises a circuit including an operational amplifier 15 to which the interruption signal from the photo interrupter 10 is fed and compared with a signal indicating a current setting of the stepping motor 7c, a direction of rotation determining unit 16 for determining a direction of rotation of the stepping motor 7c from an output of the operational amplifier 15, an absolute value calculator 17 for obtaining an absolute value of the output of the operatonal amplifier 15, voltage/frequency converter 18 to convert a voltage representing the absolute value obtained by the absolute value calculator 17 to a frequency, a valve driving unit 19 for adjusting the pinching valve 7 by driving the stepping motor 7c in the direction of rotation determined by the direction of rotation determining unit 16 at the frequency obtained by the voltage/frequency converter 18, an up/down counter 20 for counting a number of increments in up or down direction into which the stepping motor 7c has been rotated, a D/A converter for converting a digital information of the number of increments counted by the up/down counter 20 into an analog information to be fed back to the operational amplifier 15 as the signal indicating the current setting of the stepping motor 7c, and a reset signal generator 22 for generating a reset signal to be supplied to the valve driving unit 19 and the up/down counter 20 in response to the interruption signal due to the suction switch 9 at an undepressed position.

Here, the valve driving unit 19 adjusts the amount of rotational angle of the stepping motor 7c by driving the stepping motor 7c at the higher frequency when the absolute value of the difference between the interruption signal and the signal indicating the current setting of the stepping motor 7c is large, in which case the stepping motor 7c rotates by a large angle, or at a lower frequency when the absolute value of the difference between the interruption signal and the signal indicating the current setting of the stepping motor 7c is small, in which case the stepping motor 7c rotates by a small angle.

Thus, in this case, as in the previous case, an extent of opening of the pinching valve 7 is controlled in accordance with an extent of depression of the suction switch 9.

Figure 6:
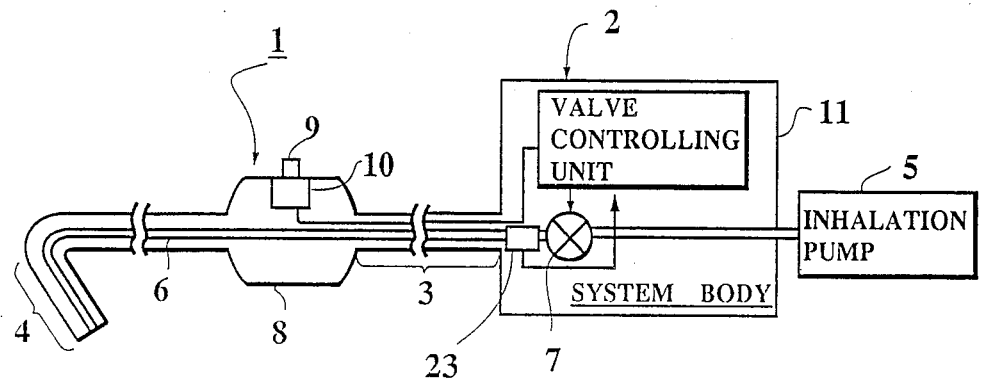
FIG. 6 is a schematic block diagram of another embodiment of an electronic endoscope system according to the present invention.

Referring now to FIG. 6, there is shown another embodiment of an electronic endoscope system according to the present invention. In the following, those parts of the system which are equivalent to the previous embodiment will be given the same reference numerals in the figures, and their explanation will be omitted.

In this embodiment, the electronic endoscope system of the previous embodiment is further equipped with a flux or pressure sensor 23 placed between the joint cord 3 and the pinching valve 7 inside the system body 2, whose detection signal is utilized as a feed back for the valve controlling unit 11, so to stabilize the flux or pressure in the suction channel 6 by controlling the extent of opening of the pinching valve 7 in accordance with the flux or pressure in the suction channel 6 as well as in accordance with an extent of depression of the suction switch 9.

In this case, if the stepping motor driven valve 7b is employed as the pinching valve 7, the valve controlling unit 11 can be constructed as follows.

Figure 7:
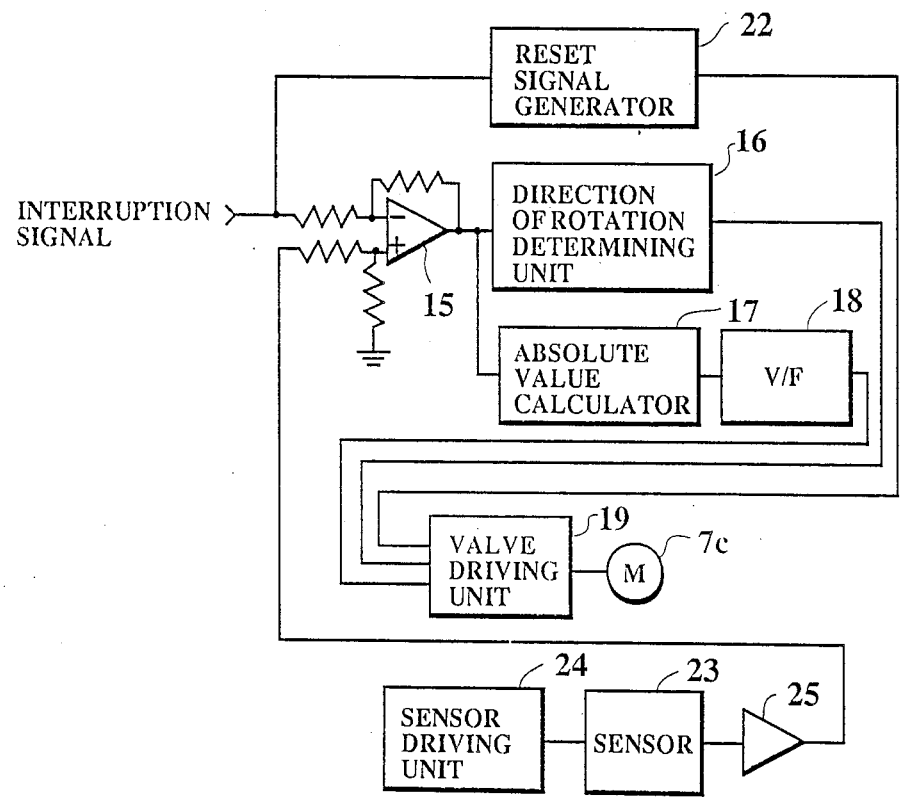
FIG. 7 is a schematic circuit diagram for a valve controlling unit in the system of FIG. 6.

Namely, as shown in FIG. 7, the valve controlling unit 11 of FIG. 5 can be modified by removing the up/down counter 20 and the D/A converter 21, and providing the flux or pressure sensor 23 for detecting the flux or pressure in the suction channel 6, a sensor driving unit 24 for activating the sensor 23, and an amplifier 25 for amplifying an output of the sensor 23. The amplified output of the sensor 23 from the amplifier 25 is fed to the operational amplifier 15 as the signal indicating the current setting of the stepping motor 7c.

Thus, acccording to this embodiment, the flux or pressure in the suction channel 6 can be stabilized by controlling the extent of opening of the pinching valve 7 in accordance with the flux or pressure in the suction channel 6 as well as in accordance with an extent of depression of the suction switch 9.

Such an additional feature is useful in removing a fluctuation in the relationship between the extent of depression of the suction switch 9 and the flux or pressure in the suction channel 6 due to structural limitations, a differrence of inner diameter of the suction channel 6, an initial instability resulting from a limited capacity of the suction pump 5, and other causes.

It is to be noted that the electromagnetic valve 7b can equally be applied to this embodiment, utilizing the output of the sensor 23 as the feed back to control the valve driver 14a in the configuration of the valve controlling unit 11 shown in FIG. 3.

It is also to be noted that the pinching valve 7 can be of any electrically driven type other than the electromagnetic one and the stepping motor driven one used in the above description of the preferred embodiments.

Besides these, many modifications and variations of the above embodiments may be made without departing from the novel and advantageous features of the present invention. Accordingly, all such modifications and variations are intended to be included within the scope of the appended claims.

What is claimed is:

1. An electronic endoscope system, comprising:
   a scope section having an end portion;
   suction pump means for providing a power for inhalation;
   suction channel means for providing a path for inhalation by the suction pump means from the end portion of the scope section;
   suction switch means to be pressed by an operator for indicating a desired strength of inhalation through the suction channel means by an extent of depression;

sensor means for detecting the extent of depression of the suction switch means;

pinching valve means, located on the suction channel means between the end portion of the scope section and the suction pump means, for adjusting a strength of inhalation through the suction channel means by adjustably changing an extent of opening; and means for controlling the strength of inhalation through the suction channel means to the desired strength of inhalation through the suction channel means indicated by the suction switch means, by adjusting the extent of opening of the pinching valve means in accordance with the extent of depression of the suction switch means detected by the sensor means.

2. The system of claim 1, where in the pinching valve means is an electromagnetic valve.

3. The system of claim 1, wherein the pinching valve means is a stepping motor driven valve in which the extent of opening of the pinching valve means is changed by a rotation of a stepping motor associated with the stepping motor driven valve.

4. The system of claim 1, further comprising additional sensor means, located on the suction channel means between the end portion of the scope section and the pinching valve means, for detecting the strength of inhalation through the suction channel means; and wherein the controlling means controls the strength of inhalation through the suction channel means to the desired strength of inhalation through the suction channel means indicated by the suction switch means, by adjusting the extent of opening of the pinching valve means in accordance with the extent of depression of the suction switch means detected by the sensor means and the strength of inhalation through the suction channel means detected by the additional sensor means.

5. The system of claim 4, wherein the additional sensor means is a flux sensor for detecting a flux of inhalation through the suction channel means.

6. The system of claim 4, wherein the additional sensor means is a pressure for detecting a pressure of inhalation through the suction channel means.

* * * * *